US005478354A

United States Patent [19]
Tovey et al.

[11] Patent Number: 5,478,354
[45] Date of Patent: Dec. 26, 1995

[54] WOUND CLOSING APPARATUS AND METHOD

[75] Inventors: H. Jonathan Tovey, Milford, Conn.; Wayne Young, Brewster, N.Y.; Peter W. J. Hinchliffe, Orange; Oleg Shikhman, Bridgeport, both of Conn.

[73] Assignee: United States Surgical Corporation, Norwalk, Conn.

[21] Appl. No.: 91,578

[22] Filed: Jul. 14, 1993

[51] Int. Cl.⁶ .................................................. A61B 17/04
[52] U.S. Cl. ........................... 606/219; 606/104; 411/457
[58] Field of Search ........................ 606/219, 220, 606/104, 150, 153, 154; 411/457, 481, 920; 227/175, 19, 901

[56] References Cited

U.S. PATENT DOCUMENTS

| | | |
|---|---|---|
| 268,632 | 12/1882 | Danforth . |
| 536,321 | 3/1895 | Turner . |
| 589,584 | 9/1897 | Swett . |
| 733,723 | 7/1903 | Lukens . |
| 1,142,510 | 6/1915 | Engle . |
| 1,801,850 | 4/1931 | Erwin . |
| 2,058,020 | 10/1936 | Jaffe . |
| 2,345,053 | 3/1944 | Judd et al. ............................ 411/920 |
| 2,384,477 | 9/1945 | Lang . |
| 2,910,067 | 10/1959 | White . |
| 2,919,621 | 1/1960 | Langdon ................................ 411/481 |
| 3,068,869 | 12/1962 | Shelden . |
| 3,385,299 | 5/1968 | Roy . |
| 3,757,629 | 9/1973 | Schneider . |
| 4,170,990 | 10/1979 | Baumgart et al. . |
| 4,407,286 | 10/1983 | Noiles et al. . |
| 4,485,816 | 12/1984 | Krumme . |
| 4,523,591 | 6/1985 | Kaplan et al. . |
| 4,592,346 | 6/1986 | Jurgutis . |
| 4,610,251 | 9/1986 | Kumar . |
| 4,708,558 | 11/1987 | Musil . |
| 4,730,971 | 3/1988 | Lin . |
| 4,744,365 | 5/1988 | Kaplan et al. . |
| 4,793,335 | 12/1988 | Frey et al. . |
| 4,887,601 | 12/1989 | Richards . |
| 5,026,390 | 6/1991 | Brown ................................... 411/920 |
| 5,089,009 | 2/1992 | Green . |
| 5,222,508 | 6/1993 | Contarini . |
| 5,246,443 | 9/1993 | Mai ........................................ 606/78 |
| 5,250,058 | 10/1993 | Miller et al. ........................ 606/153 |
| 5,366,462 | 11/1994 | Kaster et al. ........................ 606/153 |

FOREIGN PATENT DOCUMENTS

| | | | |
|---|---|---|---|
| 734439 | 5/1980 | U.S.S.R. . | |
| 1132930 | 1/1985 | U.S.S.R. ............................ 606/104 |

*Primary Examiner*—Gary Jackson

[57] ABSTRACT

An apparatus for closing trocar wounds and a method for using such apparatus. The apparatus includes a fastener having three or more legs attached to a base. The fastener is placed over a wound and its legs are embedded in tissue about the wound. In other embodiments a fastener is placed under the wound to engage fascia and skin tissue.

14 Claims, 12 Drawing Sheets

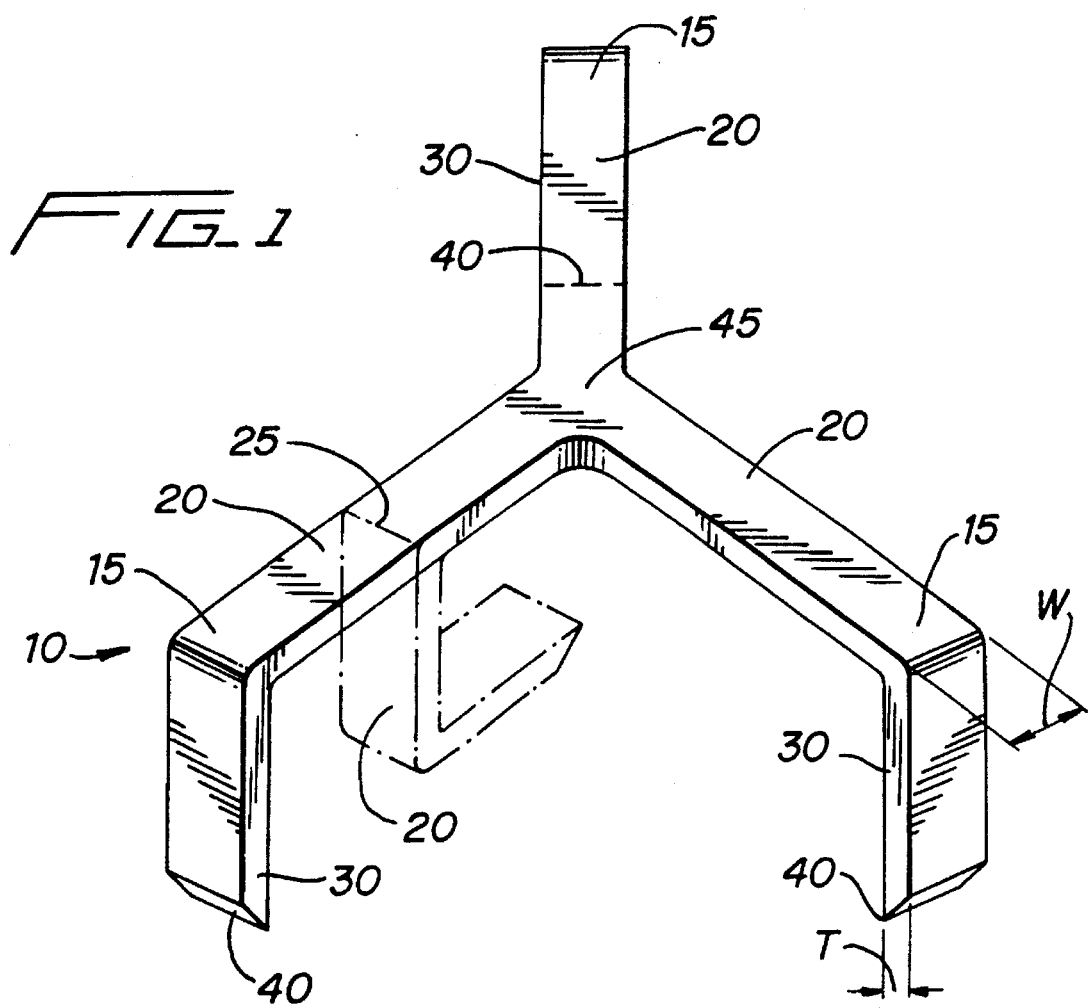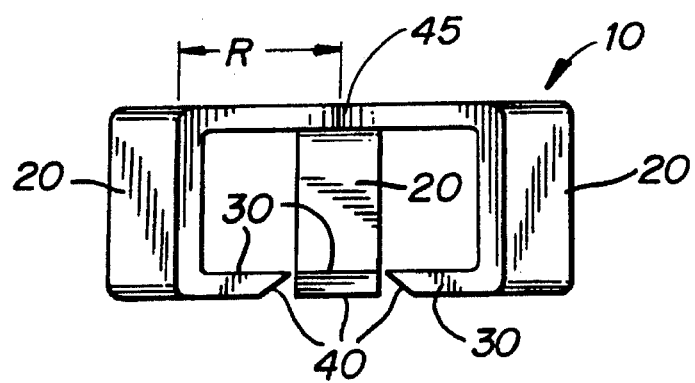

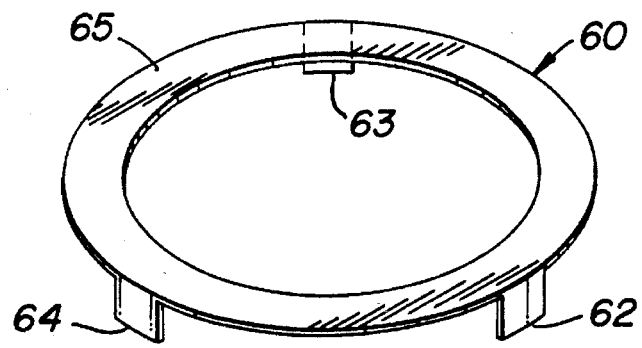
FIG_5
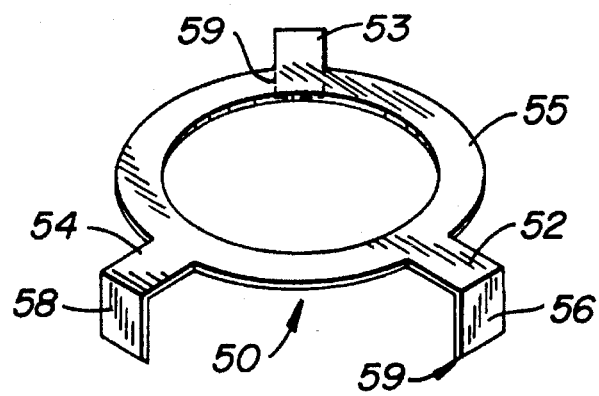
FIG_3
FIG_6
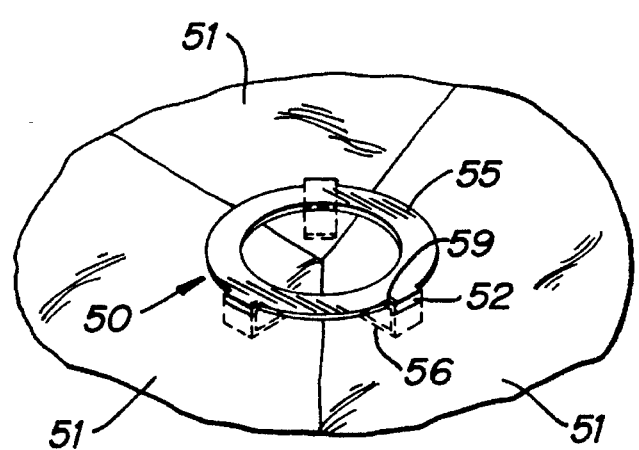

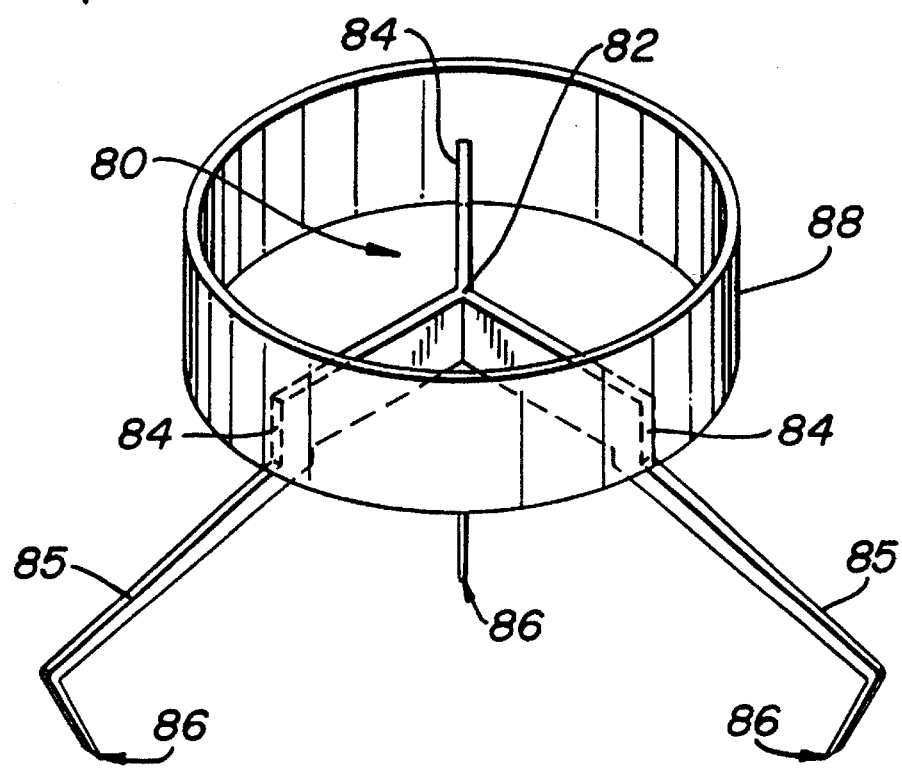
FIG_8
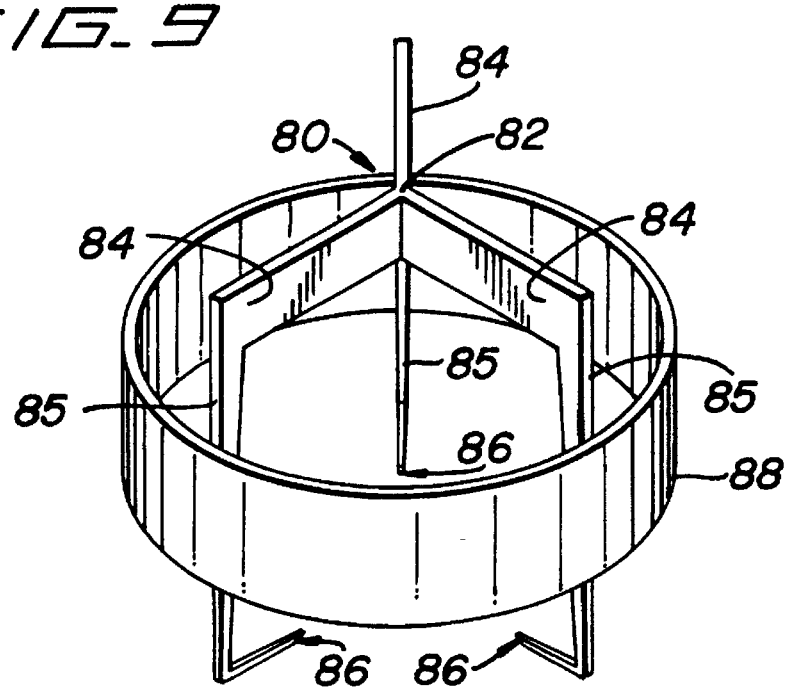
FIG_9

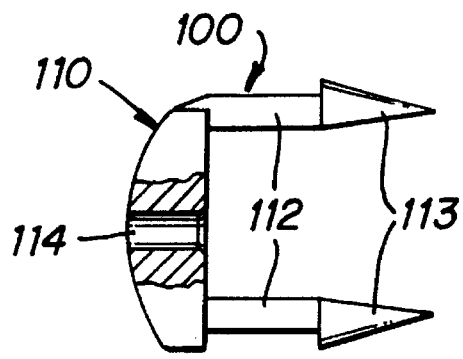
FIG._12
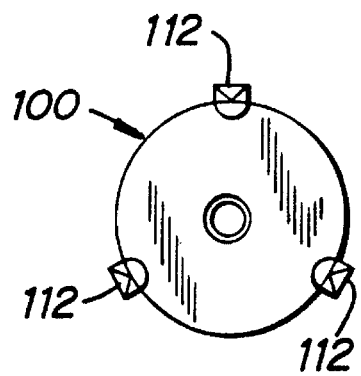
FIG._13
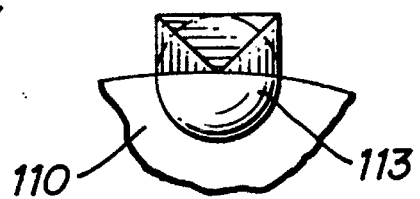
FIG._14
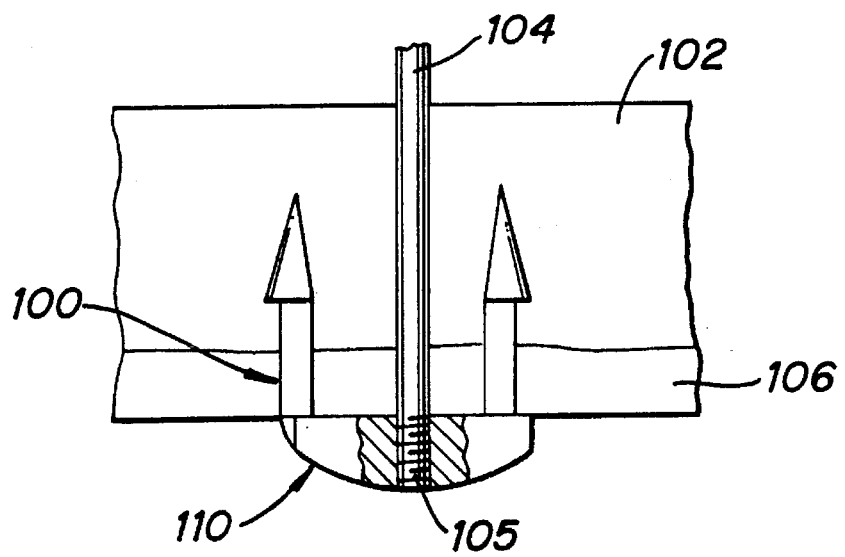
FIG._15

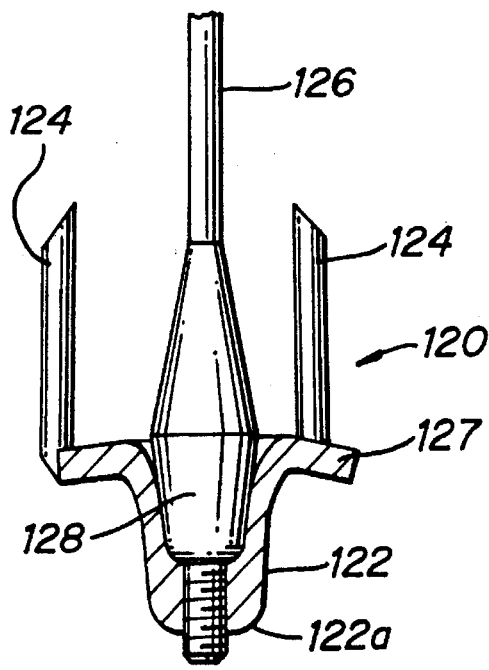
FIG_16
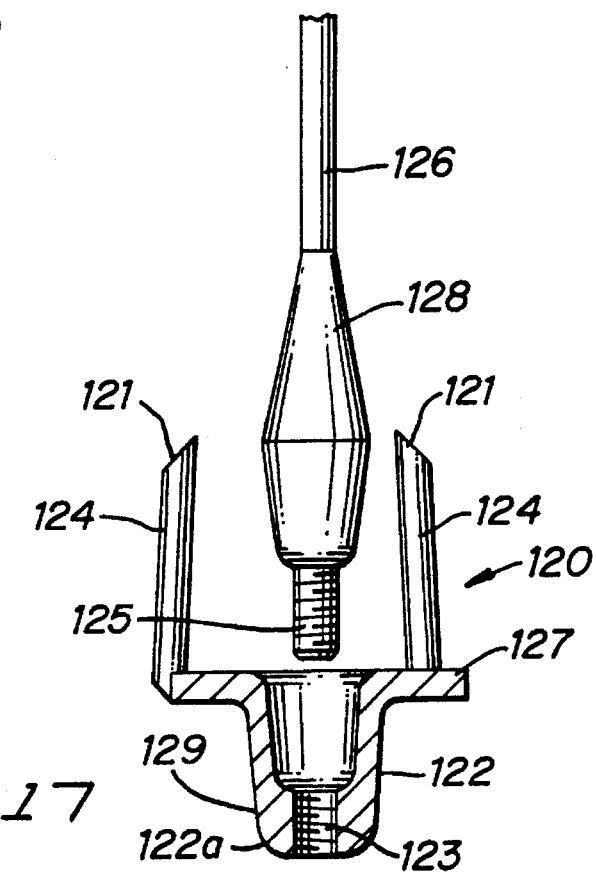
FIG_17
FIG_18
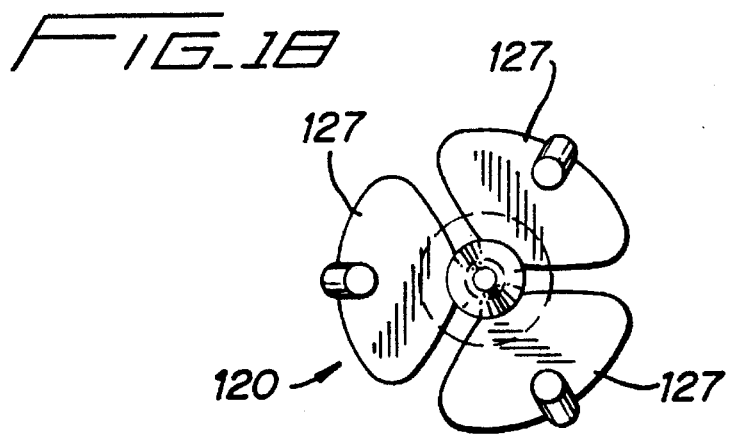

FIG._19
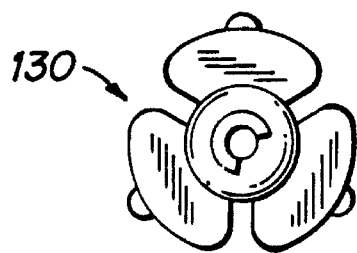
FIG._20
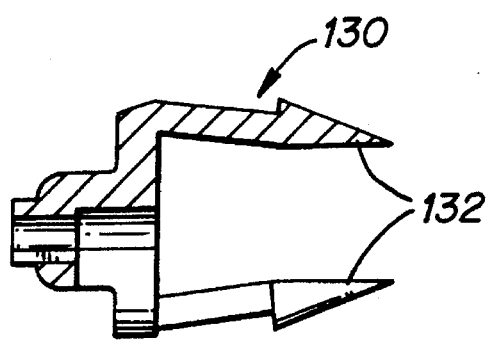
FIG._21
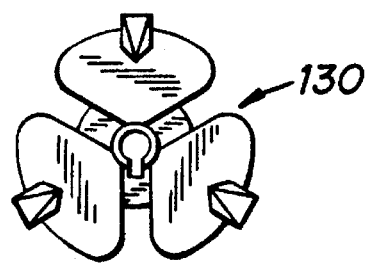

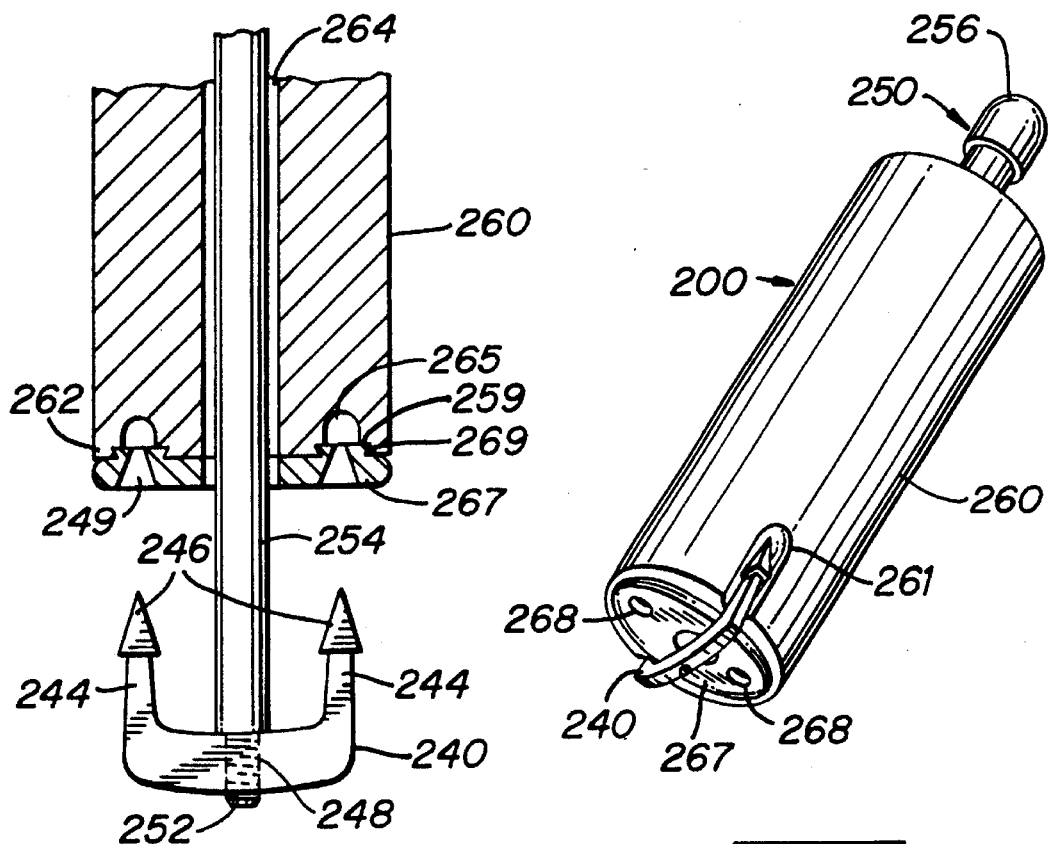
FIG. 30
FIG. 31
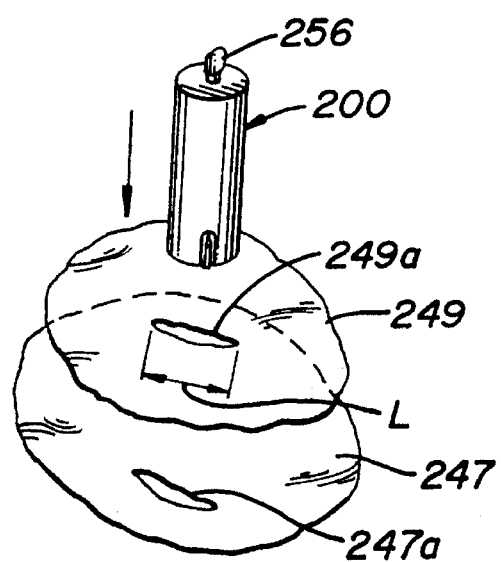
FIG. 32
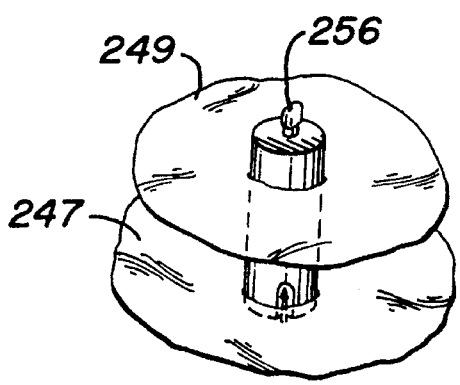
FIG. 33

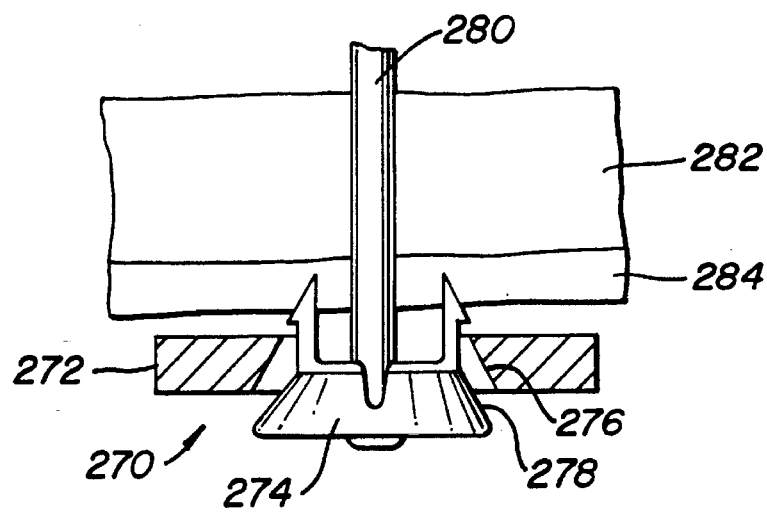
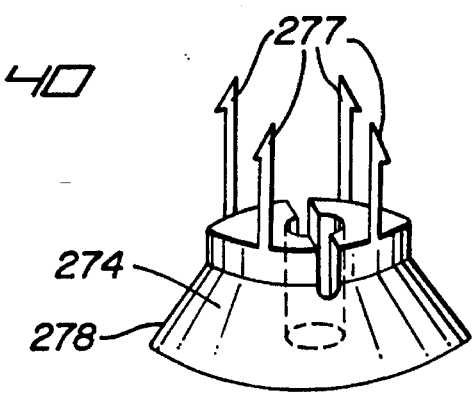
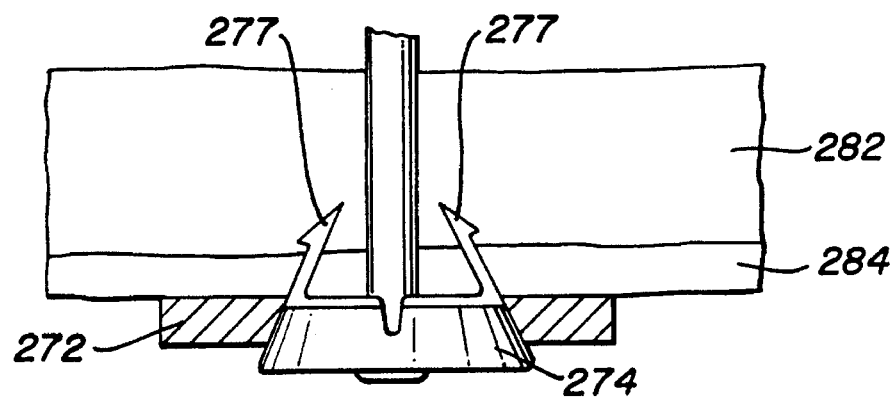

5,478,354

WOUND CLOSING APPARATUS AND METHOD

BACKGROUND OF THE INVENTION

I. Field of the Invention

The present invention relates to an improved surgical fastener for wound closure. More particularly the present invention relates to a fastener for closing a trocar incision.

II. Discussion of Background

With laparoscopic and endoscopic surgery, the small incision or puncture is made in the patient's body to provide access for a tube or a cannula (sheath) device. Once extended into the patient's body, the cannula allows for insertion of various surgical instruments such as scissors, dissectors, retractors, or biopsy instruments to perform diagnostics and/or surgery. After laparoscopic or endoscopic surgery is performed, the cannula is removed from the abdomen leaving a small incision. Typically the incision is "Y" shaped. The trocar wound may require some attention, e.g., in the form of placing sutures to close the wound.

Devices which close a wound by forming sutures from within a urethra are known. One such device is inserted into the urethra and pivotally deploys needles from which sutures are subsequently pulled through the side walls of the urethra. See, for example, Soviet Patent SU 1093329.

A variety of surgical fastener constructions and materials suitable for their manufacture are known. In addition to metals, they have been fabricated from a variety of non-bioabsorbable and bioabsorbable polymers, for example, those disclosed in U.S. Pat. Nos. 4,418,694; 4,476,865; 4,492,232; 4,512,345; 4,527,562; 4,557,263; 4,590,937; 4,620,541; 4,638,804; 4,646,741; and 4,741,337.

It would be desirable to provide a surgical fastener to close non-linear incisions, such as the triangular incisions created by commonly used trocars.

SUMMARY OF THE INVENTION

An advantage of the present invention is to provide a surgical fastener capable of closing non-linear incisions (e.g. triangular incisions) with one fastener.

Another advantage of the present invention is to provide a surgical fastener which approximates flaps of fascia tissue to each other.

The present invention provides a novel fastener for closing trocar puncture wounds. It includes a lightweight and easy to use fastener which may be employed quickly and efficiently. The fastener is easy to manufacture and is usable with currently available trocars.

In one embodiment, the surgical fastener is attached over the wound. The fastener has three or more legs that would puncture through the three "flaps" of skin about the wound, form around and inward and pull the flaps together. This firmly wedges adjacent flaps toward the center against one another. The surgical fasteners comprise a base member, and at least three legs extending from the base member.

In another embodiment, the surgical fastener is attached under the wound. The fastener comprises a base member and legs extending proximally (relative to the person applying the fastener) from the base member. This fastener is placed under fascia and the legs penetrate and secure themselves into the fascia.

The surgical fasteners of the present invention may be made of metal, e.g. stainless steel and/or titanium-containing alloy, bioabsorbable or non-bioabsorbable polymer. Specific non-bioabsorbable polymers useful for the manufacture of surgical clips are polyesters, polyamides, polycarbonates, polyvinyl chloride, polysulfones, and polypropylenes and blends or co-polymers thereof. Bioabsorbable polymers as useful for forming surgical clips include homopolymers of lactide, glycolide, caprolactone trimethylene carbonate, p-dioxanone and blends and co-polymers thereof. The metals may include shape memory alloys where a biasing action is provided to approximate tissue. Additional background on biased skin fasteners is provided in U.S. Pat. No. 5,089,009 incorporated herein by reference.

BRIEF DESCRIPTION OF THE DRAWINGS

FIG. 1 is a perspective view of a first embodiment of the surgical fastener of the present invention shown in the open, pre-application position, with a leg in closed or crimped position shown in phantom;

FIG. 2 is a side view of the surgical fastener of FIG. 1 in the closed or crimped position;

FIG. 3 is a perspective view of a second embodiment of the surgical fastener of FIG. 1, in the open pre-application position;

FIG. 5 is a perspective view of the driving means of the applier of FIG. 4;

FIG. 6 is a perspective view of the surgical fastener of FIG. 3 in the closed or crimped position;

FIG. 8 is a perspective view of a fourth embodiment of the surgical fastener of the present invention, shown in the open, pre-application position;

FIG. 9 is a perspective view of the surgical fastener of FIG. 8 shown in its closed position.

FIG. 12 is a side view of a sixth embodiment of the surgical fastener of the present invention;

FIG. 13 is a bottom view of the embodiment of FIG. 12;

FIG. 14 is an enlarged view of a portion of FIG. 13;

FIG. 15 is a side view of the surgical fastener of FIG. 10 with its legs embedded in tissue;

FIG. 16 is a side view of a seventh embodiment of the surgical fastener of the present invention with an applier having a tapered mandrel in place;

FIG. 17 is a side view of the surgical fastener of FIG. 16 with the tapered mandrel removed;

FIG. 18 is a top view of the surgical fastener of FIG. 15;

FIG. 19 is a top view of an eight embodiment of the surgical fastener of the present invention;

FIG. 20 is a side view of the surgical fastener of FIG. 19;

FIG. 21 is a bottom view of the surgical fastener of FIG. 19;

FIG. 30 is a partial cross sectional view of an eleventh embodiment of the present invention;

FIG. 31 is a perspective view of the embodiment of FIG. 30;

FIG. 32 is a perspective view of the embodiment of FIG. 30 just prior to insertion into a wound;

FIG. 33 is a perspective view of the embodiment of FIG. 30 inserted into the wound;

FIG. 39 is a side view of a fourteenth embodiment of the surgical fastener of the present invention; and FIG. 40 is a perspective view of the surgical fastener of FIG. 39;

FIG. 41 is a side view of the surgical fastener of FIG. 39 engaging tissue about a wound.

DESCRIPTION OF THE PREFERRED EMBODIMENTS

Figure 4:
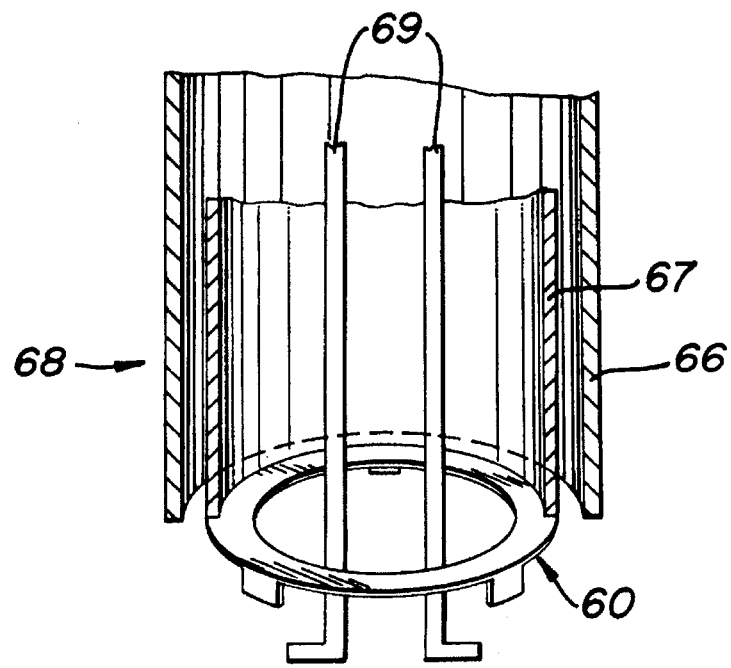
FIG. 4 is a perspective partial cross-sectional view of an applier for the surgical fastener of FIG. 3.

A first embodiment of the present invention is shown in FIG. 1. This is a surgical fastener 10 having a base member 45, three legs 15 having three leg first portions 20 integral at a first end with the base 45 and three leg second portions 30 each integral with a second end of the respective first portion 20. A barb may optionally be attached to each leg at the distal end 40 of the leg three legs second portion 30. The dimensions of the width (W) and thickness (T) are typically about that of typical skin staplers. The radius (R) is a dimension suitable for closing a trocar incision.

Leg first portions 20 are substantially coplanar with base member 45. However, leg first portions 20 may form an angle from 150 to 180 degrees with the base member. In the pre-applied position the leg second portions 30 are substantially perpendicular to the leg first portions 20. The base member 45 is the portion of the "Y" shaped section of fastener 10 which is not bent during use. A hinge region 25 is formed where leg first portion 20 is attached to base 45. FIG. 1 shows a bent leg first portion 20 in phantom.

Base member 45 optionally may be configured in any suitable shape. Such shapes include an oval shaped base 55 of fastener 50 shown in FIG. 3 or a triangular base 75 of fastener 70 shown in FIG. 7.

The surgical fastener 50 is driven from its open preapplied position as shown in FIG. 3 to its closed position of FIG. 5 by an applier 68 (shown in FIG. 4). Surgical fastener 50 has leg first portions 52, 53, 54 integral with base 55 and leg second portions 56, 57, 58 integral with leg first portions 52, 53, 54, respectively. Of course, these leg portions or base or both may be attached rather than integral if desired.

The applier 68 has a driving means 60 (pusher) having a base member 65 attached to tabs 62, 63, 64 which are positioned to distally abut the leg first portions 52, 53, 54 of the surgical fastener 50 to drive it to its closed or crimped position in tissue 51. Driving means 60 would be used together with arms 69 for holding the fastener 50 in place as leg first portions 52, 53, 54 are bent by tabs 62, 63, 64. The driving means 60 is pushed against the fastener 50 by a oval cylinder 67 located within a oval cylindrical housing 66.

Figure 7:
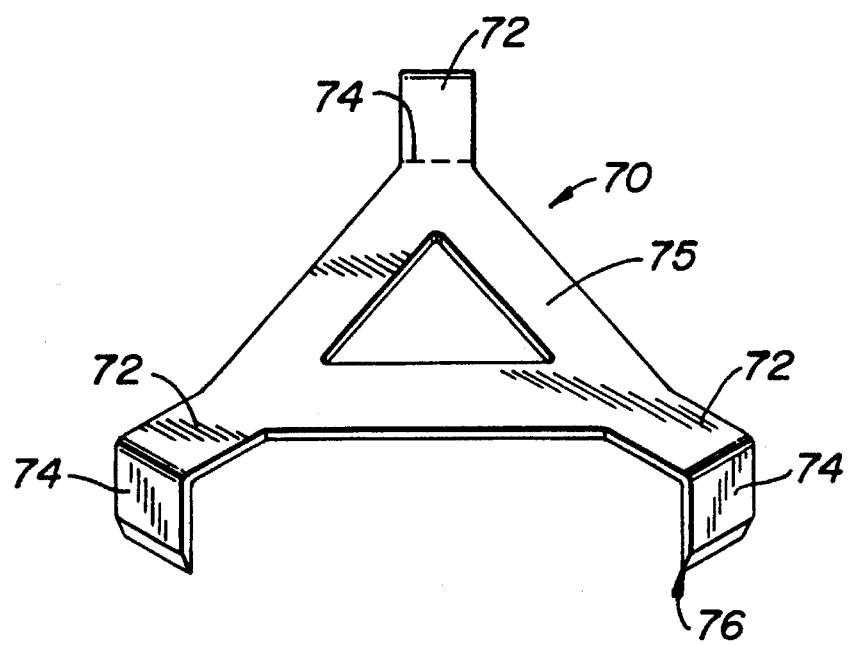
FIG. 7 is a perspective view of a third embodiment of the surgical fastener of FIG. 1 shown in the open, pre-application position.

FIG. 7 illustrates a fastener 70 with triangular base 75, three first leg portions 72 extending from the base 75, and a second leg portion 74 extending perpendicularly from each of the first leg portions, the second leg portions 74 each terminating in a tissue piercing barb, or point, 76.

The surgical fasteners of FIGS. 1–3 and 6–7 may be made of the bioabsorbable polymers, and non-bioabsorbable polymers or metals, e.g. stainless steel- or titanium-containing alloys known to those skilled in the art.

A further embodiment of the surgical fastener 80 of the present invention is illustrated in FIG. 8. This embodiment has a "Y" shaped base 82 integral with leg first portions 84. Leg first portions 84 are integral with leg second portions 85. A moveable collar 88 is initially positioned around leg first portions 84. Leg second portions 85 are integral with barbs 86. In use, the leg second portions 85 are placed so that the barbs 86 engage tissue (not shown). Then moveable collar 88 may be moved by driving means (not shown). Collar 88 is moved along leg first portions 84, and further moved to cam leg second portions 85, to a tissue approximating (closed) configuration shown in FIG. 9. Typically fastener 80 is made of metal or polymer.

Figure 10:
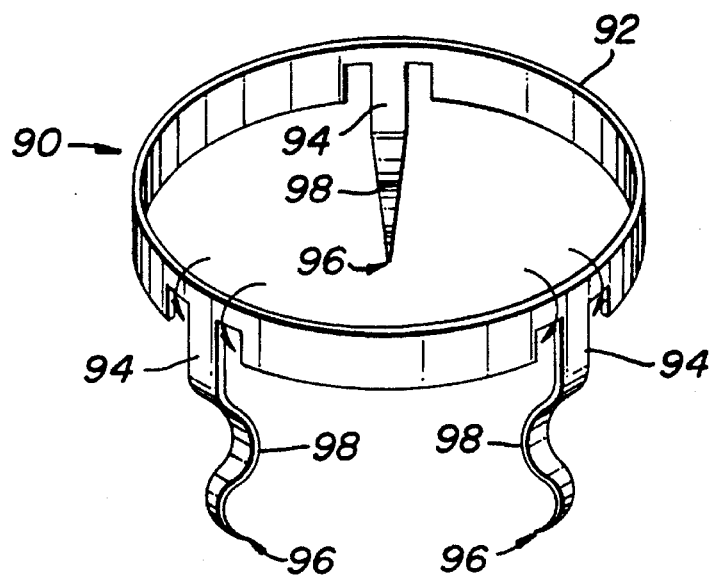
FIG. 10 is a perspective view of a fifth embodiment embodiment of the surgical fastener of the present invention in the open, pre-application position.
Figure 11:
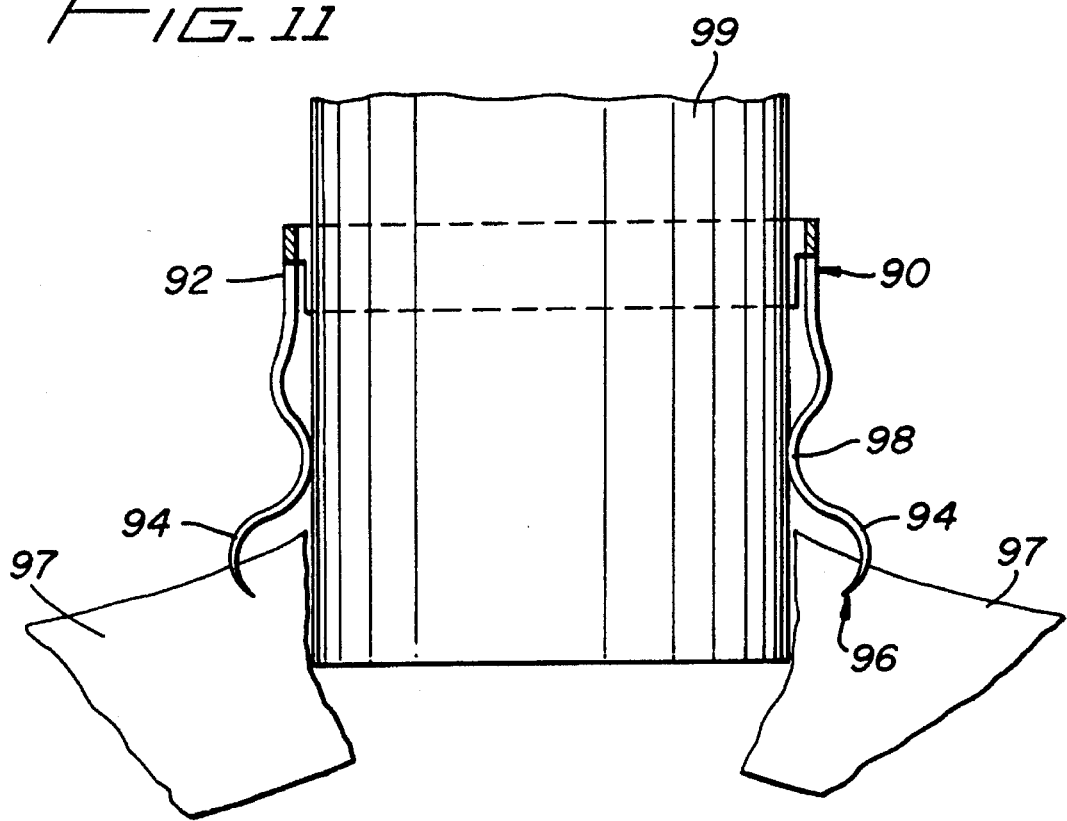
FIG. 11 is a side view of the surgical fastener of FIG. 10 in a tissue engaging position.
Figure 22:
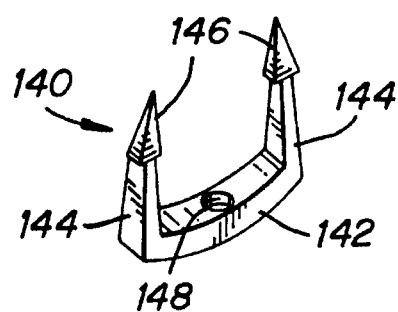
FIG. 22 is a perspective view of a ninth embodiment of the surgical fastener of the present invention.

FIGS. 10 and 11 illustrate a surgical fastener 90 configured and dimensioned to fit around the outside of a cannula assembly 99. Fastener 90 comprises a base 92 integral with legs 94. The legs 94 may be spaced a variety of distances apart but preferably are equal distances from each other. Legs 94 have camming surfaces 98 which abut cannula assembly 99. Accordingly, when fastener 90 is in contact with cannula assembly 99, its legs 94 are in an open position. Optionally, legs 94 have barbs 96. Typically fastener 90 is made of shape memory metal or polymer.

When in use, fastener 90 is driven distally along cannula assembly 99 by a driving means (not shown) or manually. A typical driving means would be a cylinder, having an inside diameter of about that of base 92, fitted about cannula assembly 99 and contacting base 92. The fastener 90 would be slid down the cannula 99 and pierced into the skin tissue 97 while simultaneously withdrawing the cannula. Fastener 90 is driven until camming surfaces 98, no longer contact the cannula 99. The fastener 90, by virtue of the torsional spring action of legs 94, would close the incision once the camming surfaces 98 no longer contact the cannula 99. This would leave legs 94 in a closed position, drawing, and thereby closing, the wound.

The fasteners of FIGS. 1–11 could be applied by an applier holding one fastener (e.g., applier 68) or by an applier (not shown) holding more than one fastener as would be developed by one skilled in the art. The fasteners of FIGS. 1–9 are permanently deformable, i.e., they can be bent from a first open position to a second closed position. The fasteners are bent from the first (open) position to the second (closed) position by application of an external force by the applier. Both positions are stable absent external forces. In contrast, only the closed position of the fastener of FIGS. 10–11 is stable. The open position is maintained by the external force of the cannula 99 pushing against the leg camming surfaces 98.

Along with these appliers, a fastener removal tool (not shown) would be employed for embodiments such as those of FIGS. 1–11. Depending on fastener configuration, the removal tool may resemble current skin stapler removal tools. However, the scissor action of such a removal tool would extract three legs instead of two legs.

FIGS. 12–15 show another embodiment of the fastener 100 of the present invention comprising a base 110 integral with legs 112. The legs 112 are each provided with a barb 113. The base has an opening 114 passing therethrough. Opening 114 is preferably threaded.

Fastener 100 is placed into a person's body through the trocar wound. Then the flaps of fascia 106 and skin tissue 102 are placed over the barbs 113 and the fastener 100 is pulled up by pulling on rod 104. Rod 104 has a threaded portion 105 which is screwed into the hole 114 of fastener 100. Fastener 100 is pulled up until the barbs engage fascia 106 and skin tissue 102, and the base 110 contacts the fascia 106.

Referring to FIG. 16, a surgical fastener 120 is provided as a single molded substantially polymeric fastener possessing three legs 124 joined at one end to a lobe 127 of a base 122. The lobes 127 are integral with a bottom portion 122a of the base 122. The base has a hole 123. Fastener 120 is molded, e.g., by injection molding, in the configuration similar or the same as shown in FIG. 17, i.e., with legs 124 and lobes 127 tilted inwardly.

Fastener 120 may be fabricated from a wide variety of polymeric materials. The principal requirement of the polymer is that it impart a sufficient spring back force to hinge region 129. Of course, the required spring back force will vary depending on the intended application of fastener 120. Suitable non-bioabsorbable polymers include polyesters, polyamides, polycarbonates, polyvinyl chloride, polysulfones, and polypropylenes. Suitable bioabsorbable polymers include trimethylene carbonate, caprolactone, and p-dioxanone, and blends thereof. Preferred bioabsorbable polymers are those described by U.S. Pat. Nos. 4,523,591 and 4,744,365, e.g., a copolymer derived from approximately 80 to 95 weight percent glycolide and 5 to 20 weight percent lactide or a two phase composition where the first phase contains 0–25% glycolide and 75–100% lactide and the second phase contains glycolide such that the overall composition contains up to 45% glycolide, incorporated herein by reference.

In use, fasteners 120 are applied with lobes 127 in a first position where they are spaced apart as shown in FIG. 16. Typically, the legs are substantially parallel in the first position. Subsequently, the lobes move to a second position in which the lobes 127 tilt towards the longitudinal axis of the fastener as shown in FIG. 17. Typically, each lobe may move up to 30 degrees, preferably up to 15 degrees, in moving from the first to second position.

Fastener 120 may be applied to tissue using a suitable applier 126 which possesses a mandrel 128 for temporarily biasing apart lobes 127 and legs 124, and for placing the open fastener 120 into position at a desired tissue wound site. Upwardly directed legs 124 are pulled up into the fascia layer of tissue and then into the skin layer about the trocar wound to pierce into the fascia and skin layers. This movement results in positioning similar to that of FIG. 15 for a different embodiment of the fastener of the present invention. The fastener 120 is pulled up until the lobes 127 contact the inner surface of the fascia tissue. Then the mandrel 128 is unscrewed from fastener 120 and removed from the tissue. This causes the legs 124 to spring inwardly to pull together the tissue flaps.

Fastener 120, as molded, may be of amorphous polymer. Optionally, the fastener undergoes a post-molding treatment, e.g. annealing, to achieve a desired degree of crystallinity and of spring back property in the hinge region.

The flexural strength of the fastener of the invention may also be increased through a post-flexing process after molding. Post-flexing involves repeatedly and temporarily biasing the legs apart through application of a temporary biasing force at an elevated temperature, e.g., 30–50 degrees C. Such post-flexing treatment lessens the internal stresses experienced by the fastener when being applied to tissue at ambient temperature.

Generally, the fastener body is sufficiently resilient to permit the legs to be deflected an angle of from 0 degrees to 30 degrees from parallel to the longitudinal axis of the fastener, and more typically an angle of from 0 degrees to 15 degrees. This angle of maximum deflection will depend on such factors as the polymeric material, the degree of crystallinity of the fastener body, the physical dimensions of the fastener body, and whether the fastener body has experienced post-flexing.

The fastener must maintain its position for a period of time sufficient to permit healing to take place, i.e., maintain its strength in vivo so as to withstand the internal pressure which is trying to force the tissue structure back open until the natural, permanent sealing of the tissue structure is complete.

Figure 23:
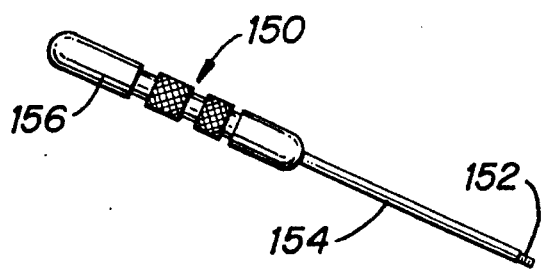
FIG. 23 is a perspective view of an applier for the surgical fastener of FIG. 22.
Figure 24:
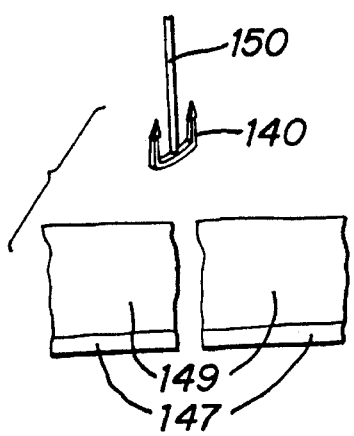
FIG. 24 is a side view of the surgical fastener of FIG. 22 just prior to insertion into a tissue wound.

FIGS. 19–21 disclose another embodiment of the fastener 130 of the present invention. This embodiment is similar to fastener 120 of FIGS. 16–18. However, its barbs 132 differ from the sharp edges 121 of the fastener 120. The fasteners 120 or 130 may be used with an applier having a tapered mandrel 128 or with an applier (as in FIG. 23) which does not employ a tapered mandrel.

FIGS. 22–28 show another embodiment of the fastener 140 of the present invention. Fastener 140 is provided with a base 142 integral with legs 144. Legs 144 each have barbs 146. The base 142 has a threaded hole 148. Prior to use, the fastener 140 is inserted with an applier (i.e., insert tool) 150. The applier 150 has a handle 156 attached to a rod 154 having an end 152 which is screw threaded. Threaded end 152 is screwed into threaded hole 148 of the fastener 140.

Figure 25:
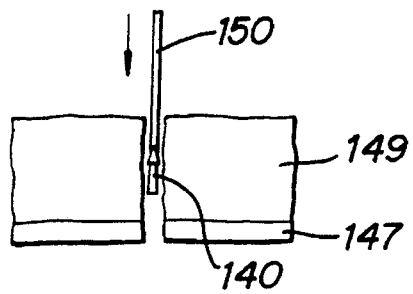
FIG. 25 is a side view of the surgical fastener of FIG. 22 being inserted into the tissue wound.
Figure 26:
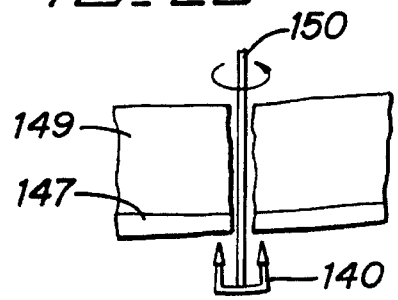
FIG. 26 is a side view of the surgical fastener of FIG. 22 passed through the tissue wound.
Figure 27:
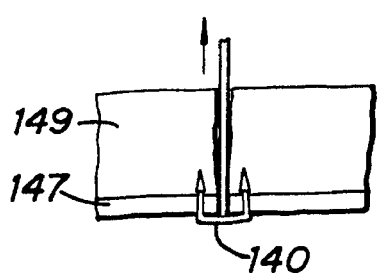
FIG. 27 is a side view of the surgical fastener of FIG. 22 engaging one side about the tissue wound, with tape securing the other side of the tissue wound.
Figure 28:
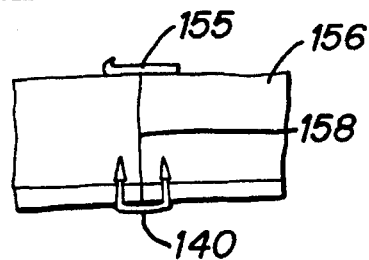
FIG. 28 is a side view of the surgical fastener of FIG. 22 engaging one side about the tissue wound with tape securing the other side of the tissue wound.

Then the fastener 140 (attached to applier 150) is inserted into a wound as shown in FIG. 25. The fastener is passed through the skin 149 and fascia 147. Then the fastener 140 is rotated 90° (as shown in FIG. 26) and pulled to engage the fascia 147 and skin 149 (as shown in FIG. 27). The applier 150 is unscrewed from the fastener 140 and removed. Then tape 155 is placed over the outer skin surface 156 of the wound 158.

Figure 29:
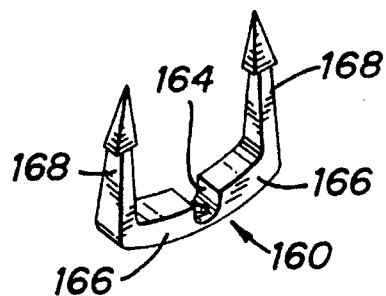
FIG. 29 is a perspective view of a portion of a tenth embodiment of a surgical fastener of the present invention which is the same as the ninth embodiment except that it is adapted to be biased.

FIG. 29 shows a tenth embodiment of the present invention. This embodiment includes a fastener 160 which is a modification of fastener 140. Fastener 160 has an indentation 164 which has a hole 162. Fastener 160 is inwardly biased as is fastener 120 and would be applied by a device such as applier 126 (FIG. 16) having a mandrel 128 for temporarily biasing apart lobes 166 and legs 168 of fastener 160.

FIGS. 30–36 show another embodiment of the present invention. This embodiment is an instrument 200 including a block 260, an applier 250, a fastener 240 and a retainer 267. Typically block 260 is elongate, has an oval transverse cross section band has a cylindrical passageway 264 passing along the longitudinal axis of the block 260. Instrument 200 also employs an applier 250 including a handle 256 attached to a rod 254 having a threaded end 252. The rod 254 passes through passageway 264 and its end 252 is threaded into a threaded bore 248 of the fastener 240. Fastener 240 also includes legs 244 attached to barbs 246. Prior to use, legs 244 are located in indentations 261 of the block 260. Instrument 200 also includes a retainer 267 having flared, raised portions 269. Flared, raised portions 269 are held within recesses 259 at the distal end 262 of block 260. The shape of portions 269 matches that of recesses 259 to releasably hold retainer 267 in place at the distal end 262 of block 260.

The distal end 262 of block 260 is also provided with indentations 265 aligned with, and in communication with the recesses 259. The receiver also has holes 249 aligned with and in communication with indentations 265.

Figure 34:
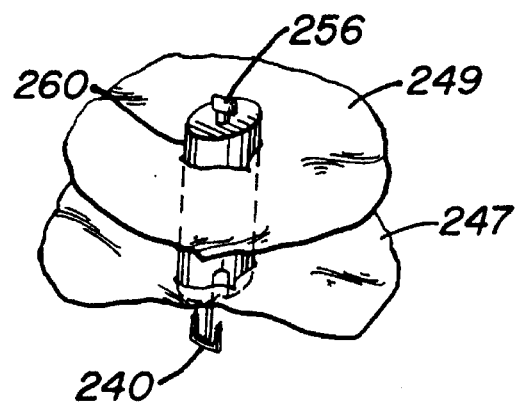
FIG. 34 is a perspective view of the embodiment of FIG. 30 turned 90° within the wound with a fastener pushed distally.
Figure 35:
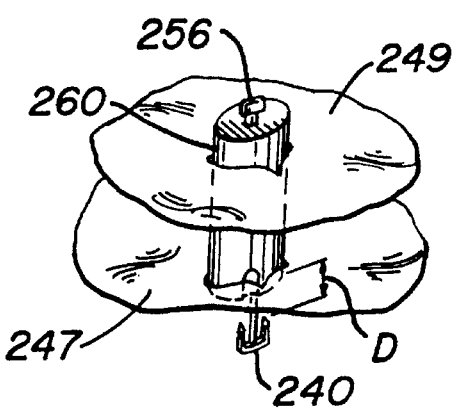
FIG. 35 is a perspective view of the embodiment of FIG. 34 with the fastener turned an additional 90°.

The instrument 200 is inserted through a wound 249a in a skin layer 249 and further inserted through a corresponding wound 247a in a fascia layer 247. Instrument 200 is inserted such that its oval shape is aligned with the length "L" of the wounds and such that its distal end is below the fascia layer 247 as shown in FIG. 33. Then instrument 200 is rotated 90° with its distal end still below the fascia layer 247. Then the fastener 240 is pushed distally out of indentations 261 as shown in FIG. 34. The instrument 200 is then pulled proximally such that the distal end 262 of block 260 is above the fascia layer 247 (but not entirely above the skin layer 249). The fastener 240 is still below the fascia layer 247 as shown in FIG. 34. Then the fastener 240 is rotated 90° to align the fastener 240 with the retainer 267 as shown in FIG. 35.

Fascia (i.e. postural fascia) of humans is about 1 mm to about 2 mm thick. Thus, in its distal most portion of FIG. 35, the fastener 240 must be separated from the retainer 267 by a longitudinal distance "D" of at least the thickness of such human fascia. Typically distance "D" ranges from about ¼ inch to about 2 inches, preferably from about ¼ inch to about 1 inch and most preferably from about ¼ inch to about ½ inch.

Figure 36:
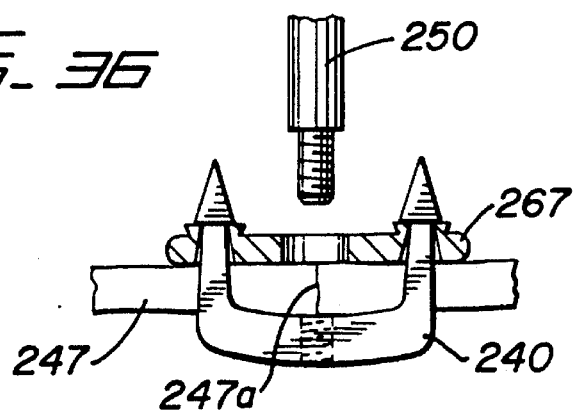
FIG. 36 is a partial cross sectional view of the embodiment of FIG. 30 wherein the fastener engages fascia and a receiver.

While maintaining the position of the block 260, the handle 256 is pulled proximally to pull fastener 240 through the fascia layer 247 and into the retainer 267 where the fastener 240 locks into the retainer 267. Then the fastener 240 and retainer 267 are pushed away from block 260 and the applier 250 is unscrewed from the fastener 240. The block 260 and applier 250 are removed from the patient. This leaves the fastener 240 locked into the retainer 267 to hold together the fascia layer 247 about wound 247a as shown in FIG. 36.

The rod 154 is preferably adapted for turning at most 90° in the direction of tightening the threaded end 152 to the fastener 140. This permits the motion to move the fastener 140 from its position in FIG. 34 to that of FIG. 35. However, rod 154 may turn in the opposite direction sufficiently to unscrew the threaded end 152 from fastener 140.

Figure 37:
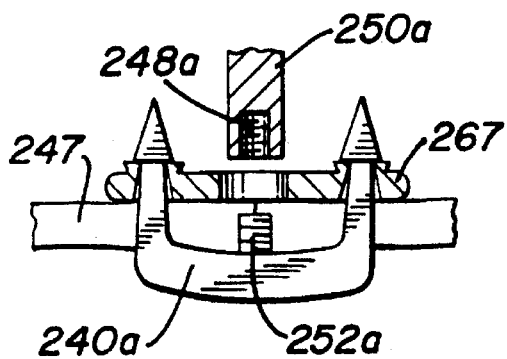
FIG. 37 is a partial cross sectional view of a twelfth embodiment of the present invention.

FIG. 37 shows a fastener 240a and applier 250a which are modified versions of fastener 240 and applier 250. The fastener 240a has a threaded portion 252a which screws into a threaded bore 248a of applier 250a. Fastener 240a is employed as in FIGS. 30–36. However, when the applier 250a is unscrewed from fastener 240a, the threaded portion 252a remains in the patient.

Figure 38:
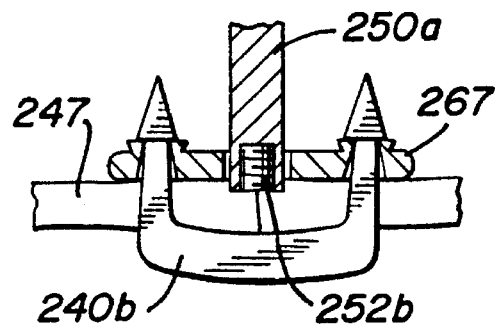
FIG. 38 is a partial cross section view of a thirteenth embodiment of the present invention.

FIG. 38 shows a fastener 240b which is a further modification of the fastener 240a. Fastener 240b is employed as is fastener 240a. However, rather than being unscrewed from rod 250a, an additional torque is applied in the screw tightening direction to break threaded portion 252b away from fastener 240b.

Other suitable means for attaching a fastener, e.g., fastener 140, to a rod, e.g. rod 154, instead of a threaded fitting may be employed. For example (not shown) a friction fit or a luerlock or otherwise releasably interlocking fastener and rod may be employed.

Another embodiment of a fastener 270 of the present invention is adapted to comprise a washer 272 fitted about a clip 274 as shown in FIGS. 39–41. The fastener 270 has four legs 277 about its circular perimeter. The inside 276 of the washer 272 is preferably tapered to match the frusto-conical shape of the clip surface 278 it contacts.

The fastener 270 is attached to a rod 280. Preferably the fastener 270 and rod-like applier 280 are screwed together. Then the fastener 270, on the end of the applier 280, is placed through a wound to below a fascia layer 284. The applier 280 is pulled upwardly to pull the fastener 270 upwardly. When the fastener 270 is pulled upwardly the legs 277 pierce the fascia 284 and skin 282 and the washer 272 contacts the fascia 284. As upward movement of the clip 274 continues, the washer 272 is pressed between the fascia 284 and the clip 274. This causes the washer 272 to cam against the sides 278 of clip 274. This camming causes the legs 277 to move towards one another. This locks the clip 274 and brings together the cut flaps of fascia 284 and skin 282 as shown in FIG. 41.

The size of the fasteners of the present invention and the tissue approximating force which the fasteners must deliver will depend on such factors as the type and size of the tissue to which it is to be applied and the size of the wound. For example, typical trocars have different diameters and thus cause different wound sizes. Because of the wide variation of trocar sizes, e.g., 3, 5, 7, 8, 10, 11, 12, 15 mm etc., it may be beneficial to manufacture two or more sizes of a given fastener. Each size would preferably cover a range of wound sizes, e.g. 8–12 mm and less than 7 mm.

Having now described the present invention and certain specific embodiments thereof, it will be readily apparent to one skilled in the art that many variations and modifications may be made to the present invention without departing from the spirit and scope thereof.

We claim:

1. A surgical fastener for closure of Y-shaped incisions, comprising:

a unitary body having a base member wherein said base member is Y-shaped and defines a plane, and piercing means for piercing and engaging body tissue, said piercing means including at least three legs, each leg extending from said base member, said legs each having a bendable hinge region and a tissue piercing point for engaging said body tissue by bending from a first position to a second position so as to present a tissue abutment surface to prevent withdrawal of the surgical fastener, and said legs each further having a proximal surface for receiving a distally directed applying force, said legs being bendable from said first position to said second position in response to application of said applying force thereto where said position is at an angle to said plane of said base, wherein said positions are stable in the absence of external forces, and wherein each of said legs has a first portion and a second portion, said first portion having a first end and a second end, said second portion having a third end and a fourth end, said first end extending from said base member, said third end extending from said second end.

2. The surgical fastener of claim 1, wherein each of said leg first portions forms an angle with said base member ranging from about 150 degrees to about 180 degrees.

3. The surgical fastener of claim 1, wherein said leg first portions are coplanar with said base member.

4. The surgical fastener of claim 1, wherein said leg first portions are substantially perpendicular to said leg second portions.

5. The surgical fastener of claim 1, wherein said fastener is formed from metal or polymer.

6. The surgical fastener of claim 1, wherein said fastener is formed from a bioabsorbable polymer.

7. The surgical fastener of claim 1, wherein said leg is bendable at a hinge region, said first end of said first leg portion and said base member form said hinge region and said first portion of said leg is bendable about said hinge region.

8. A surgical fastener for closure of a Y-shaped incision, which comprises:

a unitary body having
a) a base portion which includes three rectilinear members connected to each other in angled relationship so as to define a plane;
b) three legs, each leg extending from said base portion and being integral therewith, each said leg having a proximal surface for the reception of a distally directed applier force, and each said leg being bendable at a bendable hinge region in response to application of said applier force from a first position in which each said leg is oriented such that it is not in angled relation to the plane defined by said base portion, to a second position wherein each said leg is oriented at an angle to said plane defined by said base portion, wherein each leg includes an end portion integral therewith and oriented at an angle to its respective leg.

9. The surgical fastener of claim 8 wherein said rectilinear members of said base portion define a triangular shaped configuration.

10. The surgical fastener of claim 9 wherein said legs in said first position are oriented within said plane defined by said base portion.

11. The surgical fastener of claim 8 wherein said rectilinear members of said base portion define a Y-shaped configuration.

12. The surgical fastener of claim 11 wherein said legs in said first position are oriented within said plane defined by said base portion.

13. The surgical fastener of claim 11 wherein said legs in said first position define a plane which is parallel to said plane defined by said base portion.

14. The surgical fastener of claim 8 wherein said end portions of said legs each possess a tissue piercing tip and a tissue abutment surface for preventing withdrawal of said surgical fastener from body tissue.

* * * * *